United States Patent
Kuroda et al.

(10) Patent No.: US 10,932,831 B2
(45) Date of Patent: Mar. 2, 2021

(54) BONE PLATE AND BONE PLATE SYSTEM

(71) Applicant: OLYMPUS TERUMO BIOMATERIALS CORP., Tokyo (JP)

(72) Inventors: Koichi Kuroda, Kanagawa (JP); Mitsuya Urata, Kanagawa (JP)

(73) Assignee: OLYMPUS CORPORATION, Tokyo (JP)

(*) Notice: Subject to any disclaimer, the term of this patent is extended or adjusted under 35 U.S.C. 154(b) by 225 days.

(21) Appl. No.: 16/180,128

(22) Filed: Nov. 5, 2018

(65) Prior Publication Data

US 2019/0069937 A1    Mar. 7, 2019

Related U.S. Application Data

(63) Continuation of application No. PCT/JP2016/064069, filed on May 11, 2016.

(51) Int. Cl.
*A61B 17/80* (2006.01)
*A61B 17/17* (2006.01)
A61B 17/86 (2006.01)

(52) U.S. Cl.
CPC ...... *A61B 17/8052* (2013.01); *A61B 17/1728* (2013.01); *A61B 17/80* (2013.01);
(Continued)

(58) Field of Classification Search
CPC . A61B 17/8052; A61B 17/1728; A61B 17/80; A61B 17/809; A61B 17/8033; A61B 17/8605; A61B 17/8095
See application file for complete search history.

(56) References Cited

U.S. PATENT DOCUMENTS 6,193,721 B1 *   2/2001   Michelson ......... A61B 17/1604
                                                606/246
6,623,486 B1 *   9/2003   Weaver ............. A61B 17/8057
                                                606/281
(Continued)

FOREIGN PATENT DOCUMENTS

EP      1 250 892 A2    10/2002
EP      2 623 057 A1    8/2013
(Continued)

OTHER PUBLICATIONS

Extended Supplementary European Search Report dated Dec. 3, 2019 in European Patent Application No. 16 90 1655.7.
(Continued)

*Primary Examiner* — Kevin T Truong
*Assistant Examiner* — Tracy L Kamikawa
(74) *Attorney, Agent, or Firm* — Scully, Scott, Murphy & Presser, P.C.

(57) ABSTRACT

A bone plate includes: a band-shaped body section that is fixed along a longitudinal direction of the tibia; a transverse section that is fixed along a direction intersecting the longitudinal direction of the tibia; a joining section for joining the body section and the transverse section; and screw holes. The body section, the joining section, and the transverse section have a curved surface shape, a first plane on which the axial line of a screw hole in the joining section is disposed and a second plane on which the axial line of a screw hole in the body section is disposed are substantially parallel to each other, the angles between a straight line connecting a longitudinal direction upper-end portion and lower-end portion of the bone plate and the first plane and the second plane are predetermined angles, and an axial line and an axial line are at twisted positions.

13 Claims, 12 Drawing Sheets

(52) U.S. Cl.
CPC ........ *A61B 17/809* (2013.01); *A61B 17/8033* (2013.01); *A61B 17/8605* (2013.01)

(56) References Cited

U.S. PATENT DOCUMENTS

| | | | |
|---|---|---|---|
| 7,951,176 B2* | 5/2011 | Grady, Jr. | A61B 17/746 606/280 |
| 8,317,842 B2* | 11/2012 | Graham | A61B 17/1739 606/286 |
| 2002/0156474 A1 | 10/2002 | Wack et al. | |
| 2004/0030339 A1 | 2/2004 | Wack et al. | |
| 2004/0059334 A1 | 3/2004 | Weaver et al. | |
| 2004/0059335 A1 | 3/2004 | Weaver et al. | |
| 2005/0049594 A1 | 3/2005 | Wack et al. | |
| 2005/0080421 A1 | 4/2005 | Weaver et al. | |
| 2006/0195099 A1 | 8/2006 | Bottlang | |
| 2008/0132960 A1 | 6/2008 | Weaver et al. | |
| 2009/0143825 A1 | 6/2009 | Graham et al. | |
| 2012/0029579 A1 | 2/2012 | Bottlang et al. | |
| 2012/0215265 A1 | 8/2012 | Bottlang | |
| 2012/0323284 A1 | 12/2012 | Baker et al. | |
| 2013/0006312 A1 | 1/2013 | Graham et al. | |
| 2013/0079832 A1 | 3/2013 | Bottlang | |
| 2013/0211463 A1 | 8/2013 | Mizuno et al. | |
| 2014/0121710 A1 | 5/2014 | Weaver et al. | |
| 2014/0277178 A1 | 9/2014 | O'Kane et al. | |
| 2014/0358185 A1 | 12/2014 | Bottlang et al. | |
| 2016/0074081 A1 | 3/2016 | Weaver et al. | |
| 2017/0007304 A1 | 1/2017 | Kuroda et al. | |
| 2017/0027627 A1 | 2/2017 | Paik | |
| 2017/0215931 A1* | 8/2017 | Cremer | A61B 17/80 |
| 2018/0296256 A1* | 10/2018 | Beckett | A61B 17/7216 |

FOREIGN PATENT DOCUMENTS

| | | |
|---|---|---|
| EP | 3 123 971 A1 | 2/2017 |
| EP | 3 132 762 A1 | 2/2017 |
| JP | 4368560 B2 | 11/2009 |
| JP | 2012-066017 A | 4/2012 |
| JP | 2014-050722 A | 3/2014 |
| JP | 2014-513999 A | 6/2014 |
| JP | 2014-522673 A | 9/2014 |
| JP | 2015-524316 A | 8/2015 |
| WO | 2001/19267 A1 | 3/2001 |
| WO | 2009/073405 A2 | 6/2009 |
| WO | 2012/116819 A1 | 9/2012 |
| WO | 2012/174385 A2 | 12/2012 |
| WO | 2014/160699 A1 | 10/2014 |
| WO | 2015/146866 A1 | 10/2015 |
| WO | 2015/160022 A1 | 10/2015 |

OTHER PUBLICATIONS

International Search Report dated Aug. 9, 2016 issued in International Application No. PCT/JP2016/064069.
Japanese Office Action dated Apr. 28, 2020 in Japanese Patent Application No. 2018-516275.

* cited by examiner

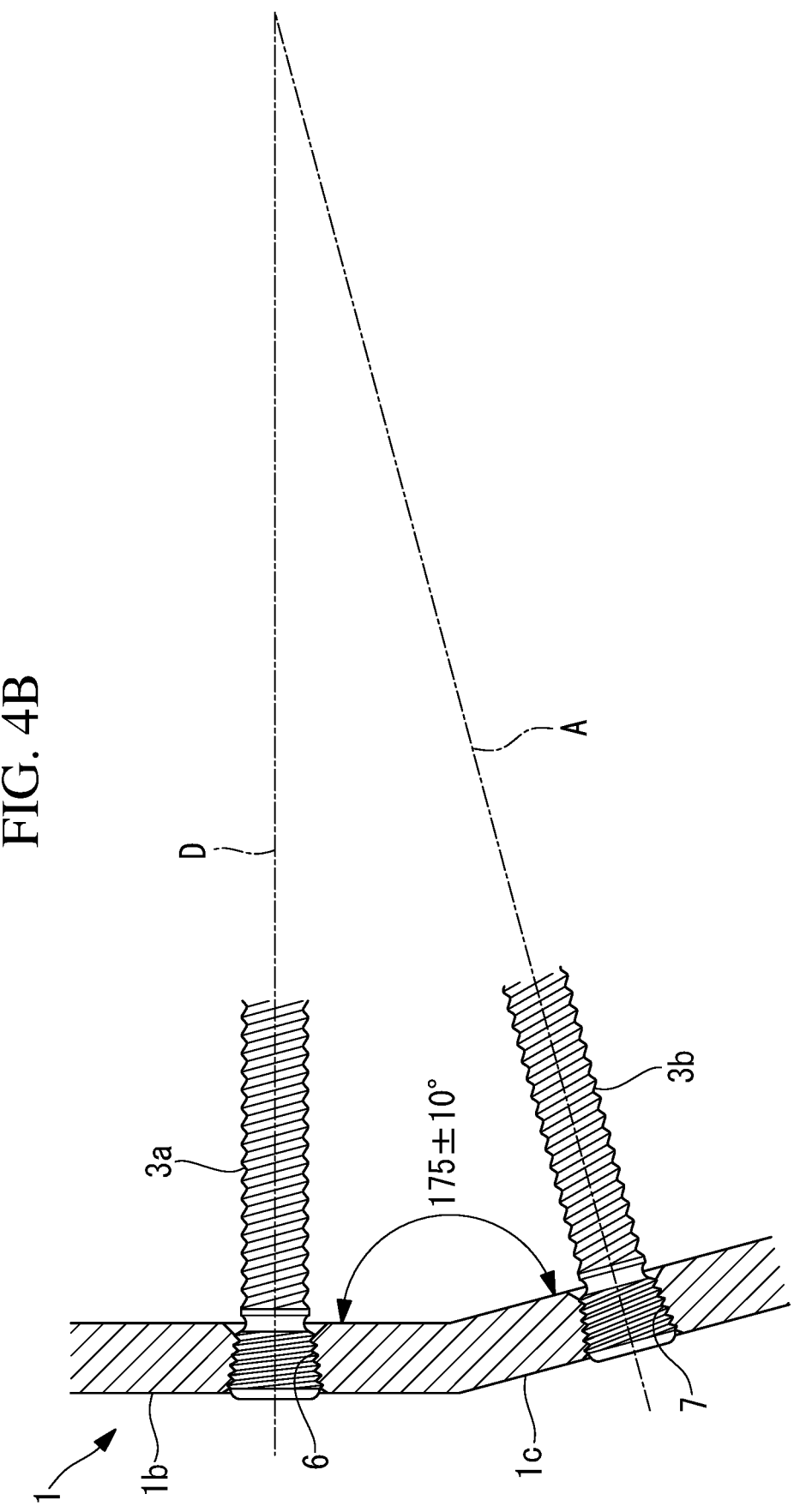

BONE PLATE AND BONE PLATE SYSTEM

CROSS-REFERENCE TO RELATED APPLICATIONS

This is a continuation of International Application PCT/JP2016/064069, with an international filing date of May 11, 2016, which is hereby incorporated by reference herein in its entirety.

TECHNICAL FIELD

The present invention relates to a bone plate and a bone plate system.

BACKGROUND ART

In order to fix a site of a bone fracture or osteotomy and to promote bone curing and osteosynthesis, a bone plate system having a bone plate and screws for fixing this bone plate to the bone has been used (refer to, for example, PCT International Publication No. WO2015/146866).

Such a bone plate system is used for, for example, high tibial osteotomy (HTO) of gonarthrosis. High tibial osteotomy is surgery for correcting the direction of load biased towards the inner side due to bow leg deformity by cutting the patient's own bone to slightly change the angle and by performing alignment, thus shifting the direction of the load towards the outer side.

Several types of high tibial osteotomy are known, such as: an open wedge HTO method in which the bone is cut from the inner side towards the outer side of the tibia, the cut is dilated, and, for example, a trapezoidal or wedge-shaped artificial bone is inserted to correct the angle; and a closed wedge HTO method in which the bone is cut off into a wedge shape from the outer side of the tibia, and the cut is shrunk to correct the angle.

PCT International Publication No. WO2015/146866 disclose a bone plate system used mainly for the open wedge method. In high tibial osteotomy based on the open wedge method, the bone is notched from the inner side towards the outer side of the tibia, a substantially wedge-shaped artificial bone is inserted into a dilated section, which is the notch that has been dilated, and then a bone plate is placed so as to span this dilated section. The bone plate placed in this manner is fixed to the tibia with screws.

Publication of Japanese Patent No. 4368560 discloses a bone plate system that is used to remedy and fix the site of a bone fracture when a long bone, such as the femur or the tibia, is broken. In the bone plate system in Publication of Japanese Patent No. 4368560, the axial directions of the screws can be changed by rotation when the bone plate is to be fixed to the epiphyseal region with screws.

SUMMARY OF INVENTION

One aspect of the present invention is a bone plate including: a band-shaped body section that is fixed along a longitudinal direction of a tibia; a transverse section that is fixed along a direction intersecting the longitudinal direction of the tibia; a joining section for joining the body section and the transverse section; and a plurality of screw holes that are arranged in the transverse section, the body section, and the joining section in a manner spaced apart from one another and that pass therethrough in a plate thickness direction, wherein the plurality of screw holes include a first screw hole provided in the joining section and a second screw hole provided in the body section, the body section, the joining section, and the transverse section have a curved surface shape that continues in such a manner as to twist about an axial line along the longitudinal direction of the tibia, a first plane on which an axial line of the first screw hole is disposed and a second plane on which an axial line of the second screw hole is disposed are substantially parallel to each other, the angles between a straight line connecting a longitudinal-direction upper-end portion and lower-end portion in the bone plate and the first plane and the second plane are predetermined angles, and the axial line of the first screw hole and the axial line of the second screw hole are disposed at twisted positions.

Another aspect of the present invention is a bone plate system including: any one of the above-described bone plats; and a plurality of screws that are tightened into the plurality of screw holes in the bone plate to fix the bone plate to the tibia.

BRIEF DESCRIPTION OF DRAWINGS

FIG. 4B is a partially magnified view showing, in more detail, a tilting relationship in a side view of the transverse section and the joining section.

DESCRIPTION OF EMBODIMENTS

A bone plate 1 and a bone plate system 2 according to one embodiment of the present invention will now be described with reference to the drawings.

Figure 1A:
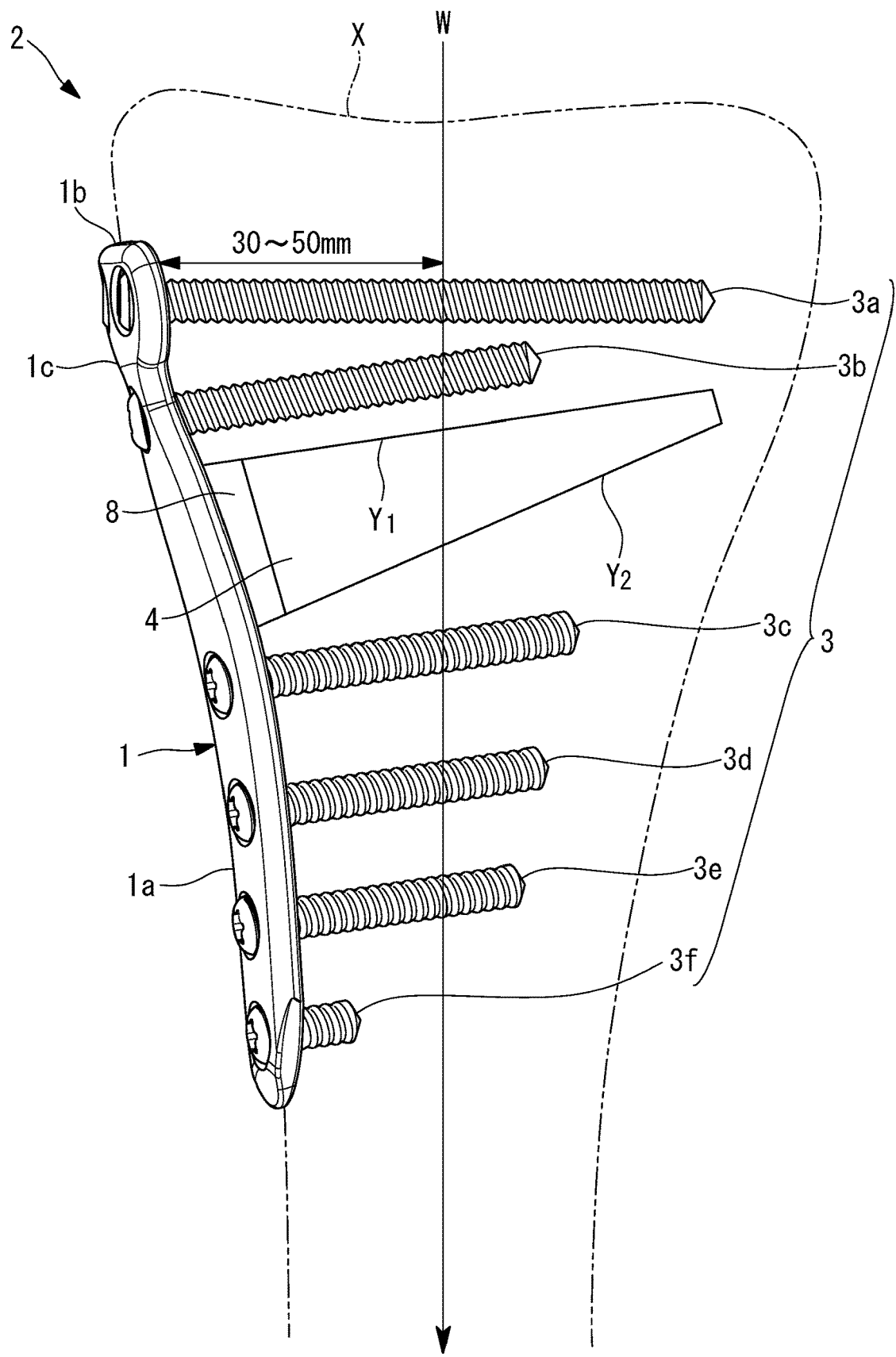
FIG. 1A is an overall view showing a bone plate system according to one embodiment of the present invention.

As shown in FIG. 1A, the bone plate system 2 according to this embodiment includes: the bone plate 1; a plurality of screws 3 for fixing this bone plate 1 to a high side surface of a tibia X; and an artificial bone 4 inserted into a notch formed from the inner side surface side towards the outer side of the tibia X.

The bone plate 1 according to this embodiment is an elongated band-shaped member that is fixed to a high inner side surface of the tibia X after osteotomy for high tibial osteotomy of gonarthrosis and has a subtlety curved shape in conformance to a typical surface shape of the tibia X so as to run along the curved surface shape of the side surface thereof at a position changing from the diaphyseal region towards the epiphyseal region of the tibia X.

Figure 2A:
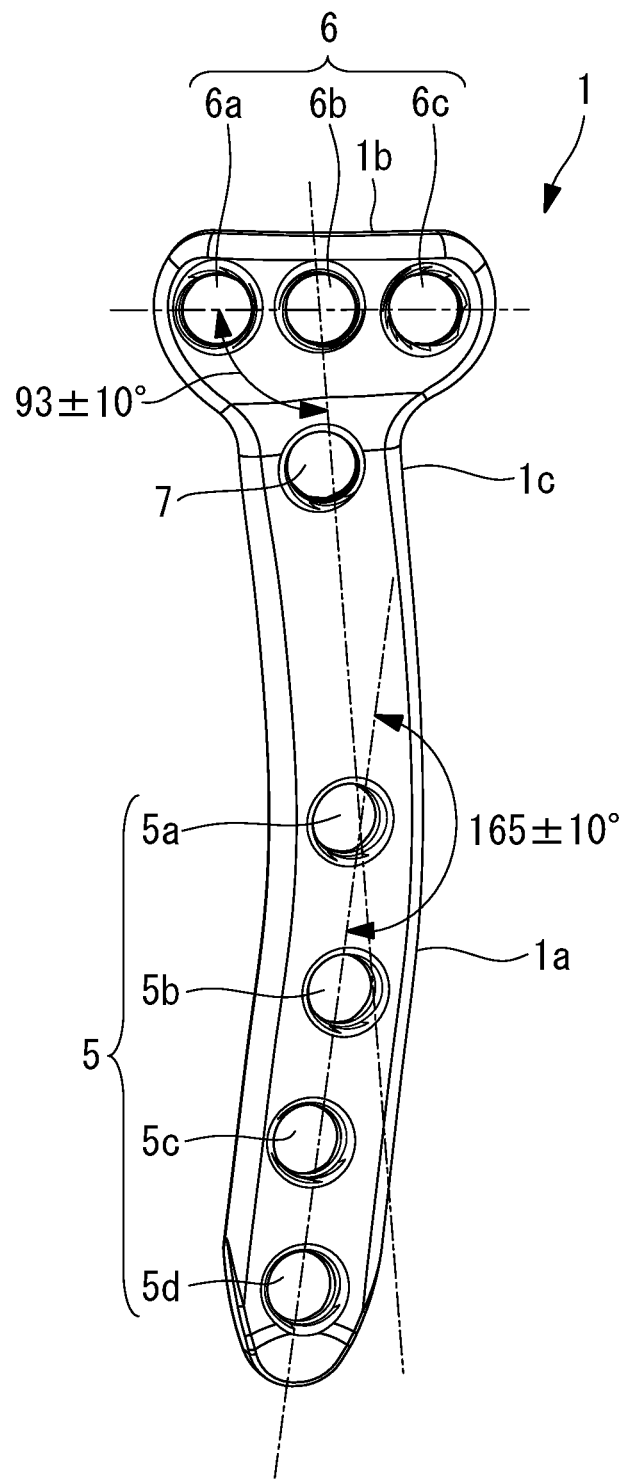
FIG. 2A is a front view showing a bone plate according to one embodiment of the present invention used in the bone plate system in FIG. 1A.
Figure 2B:
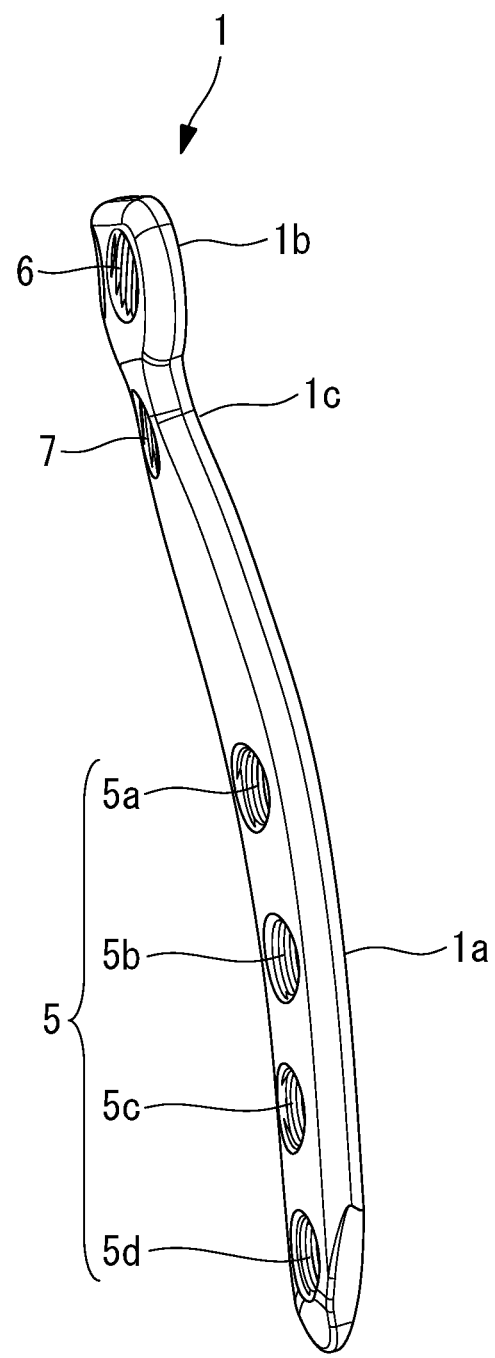
FIG. 2B is a side view showing the bone plate in FIG. 2A.
Figure 2C:
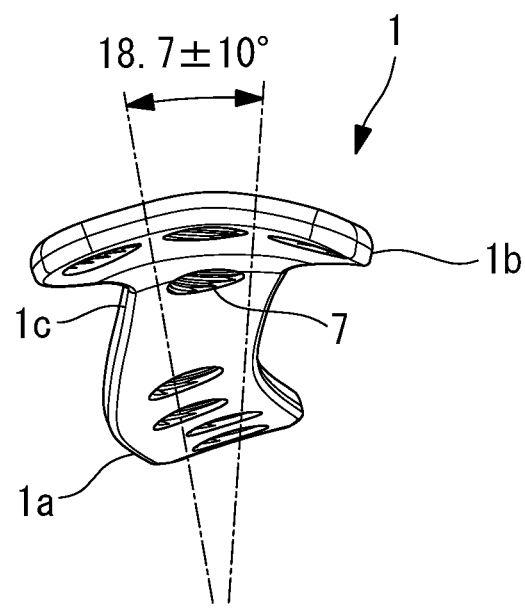
FIG. 2C is a front view showing the bone plate in FIG. 2A.

As shown in FIGS. 2A, 2B, and 2C, this bone plate 1 includes: an elongated band-shaped body section 1a; a transverse section 1b extending in a direction intersecting the longitudinal direction of this body section 1a; and a joining section 1c for linking the body section 1a and the transverse section 1b, and the bone plate 1 is formed to be substantially T shaped as a whole. As shown in FIG. 2C, the joining section 1c is shaped in such a manner as to bend in one direction from one end of the body section 1a and twist (the twist angle is 18.7°±10°) about the longitudinal axis of the body section 1a towards the transverse section 1b at the leading end. The body section 1a is substantially arch shaped in a cross section that is curved with a predetermined curvature along the shape of the tibia X.

As shown in FIG. 2A, the body section 1a of the bone plate 1 includes a plurality of screw holes 5 provided in a manner spaced apart from one another in the longitudinal direction. FIG. 2A shows an example in which four screw holes 5a, 5b, 5c, and 5d are provided in the body section 1a. The transverse section 1b includes a plurality of screw holes 6 provided in a manner spaced apart from one another in a direction intersecting the longitudinal direction of the body section 1a. FIG. 2A shows an example where three screw holes 6a, 6b, and 6c are provided in the transverse section 1b. The joining section 1c includes one screw hole 7 disposed in a manner spaced apart from the screw holes 5 and 6 (6b) in the above-described longitudinal direction.

Figure 3:
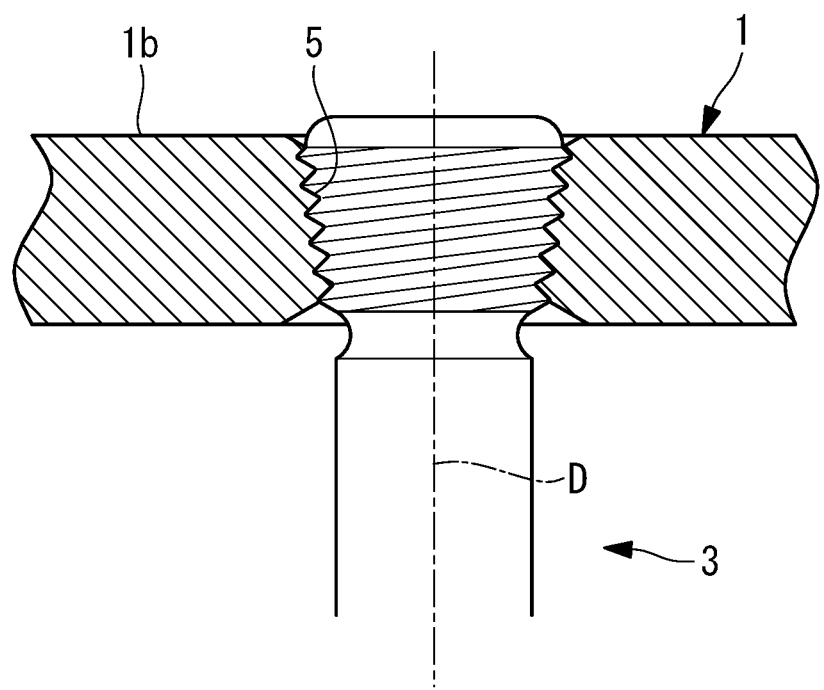
FIG. 3 is a partial longitudinal sectional view showing the relationship between a screw hole provided in the bone plate in FIG. 2A and a screw.

As shown in FIG. 3, the screws 3a are inserted into the screw holes 5, 6, and 7 from one end towards the other end in the plate thickness direction. At this time, axial lines D of the screws 3 are orthogonal to the plate surface of the bone plate 1.

Although FIG. 3 shows an example case of a screw hole 6 in the transverse section 1b, the screw holes 5 and 7 in the body section 1a and the joining section 1c also have the same structure.

Screws 3c and 3e are inserted into the screw holes 5a and 5c, respectively, provided in the body section 1a, and a screw 3b is inserted into the screw hole 7 provided in the joining section 1c. Screws 3a are inserted into the screw holes 6a, 6b, and 6c in the transverse section 1b.

Figure 1B:
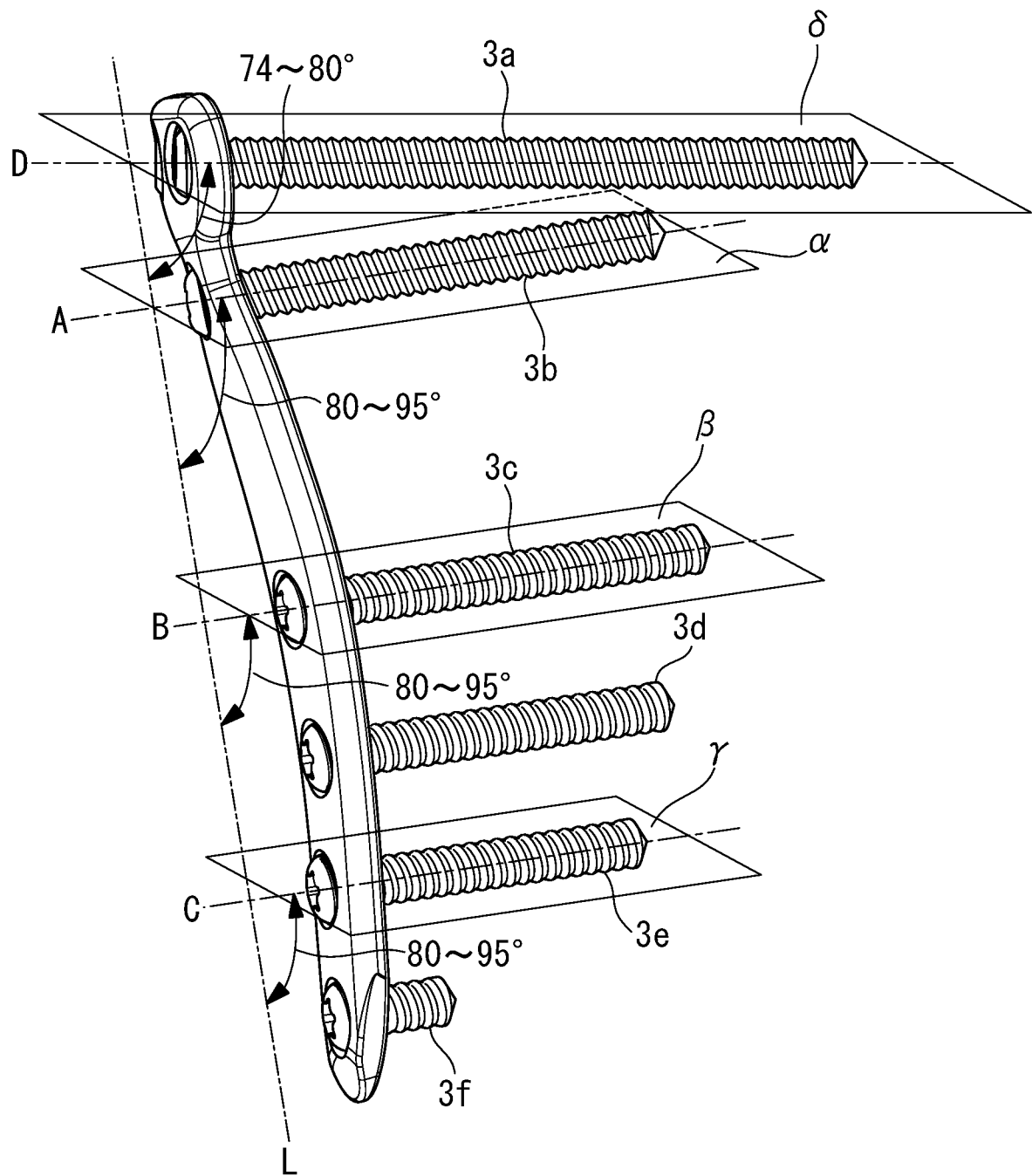
FIG. 1B is an overall view showing the positional relationship between the bone plate in FIG. 1A and screws inserted into screw holes provided in the bone plate.
Figure 1C:
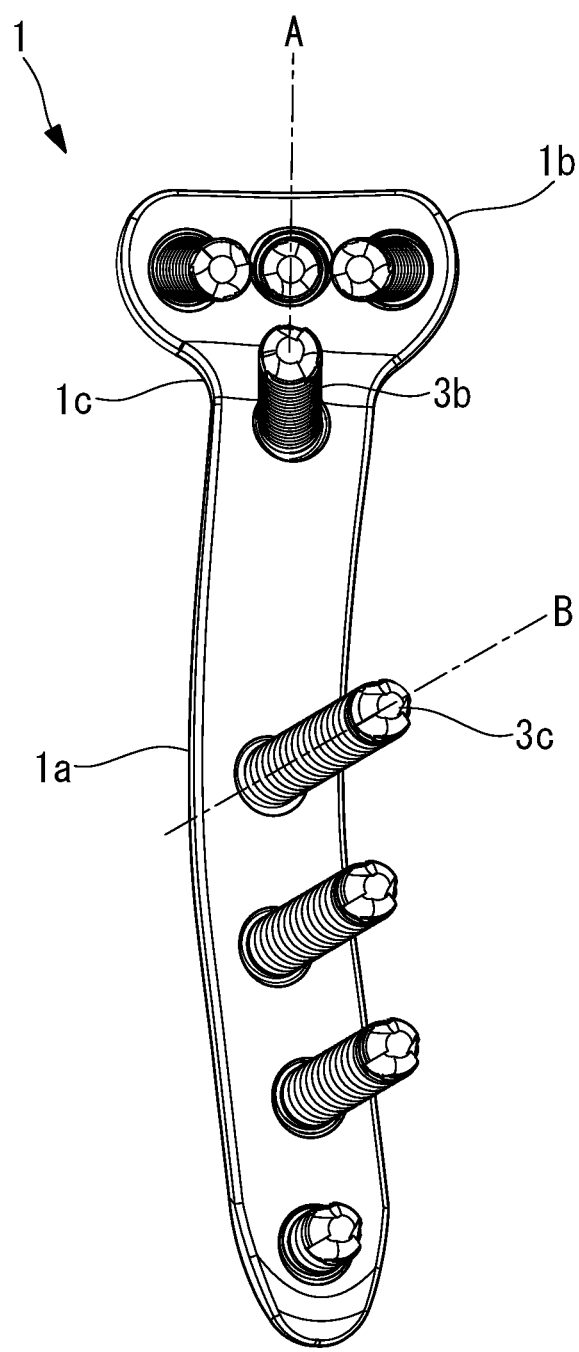
FIG. 1C is a plan view showing the positional relationship between the bone plate in FIG. 1A and screws inserted into screw holes provided in the bone plate.

At this time, as shown in FIG. 1B, an axial line A of the screw 3b is disposed on a first plane α tilted relative to a fourth plane δ including a straight line that specifies the arrangement direction of the screw holes 6a, 6b, and 6c and the axial lines D of the screws 3a inserted into the screw holes 6a, 6b, and 6c, respectively. Also, an axial line B of the screw 3c and an axial line C of the screw 3e are disposed on a second plane β and a third plane γ, respectively, that are substantially parallel to the first plane α. Furthermore, as shown in FIG. 1C, because the axial line A of the screw 3b and the axial line B of the screw 3c are disposed at positions twisted relative to each other, not only do the axial line A of the screw 3b and the axial line B of the screw 3c that are projected on the articular surface of the tibia X intersect each other, but also the axial line A and the axial line B are substantially parallel to each other when the tibia X provided with the bone plate 1 is viewed from the front or the back.

As shown in FIG. 1B, the bone plate 1 is designed so that the angle between a straight line L connecting a longitudinal-direction upper-end portion and lower-end portion of the bone plate 1 and the first plane α; the angle between the straight line L and the second plane β; and the angle between the straight line L and the third plane γ are each 80° to 95° inclusive, preferably 84° to 91° inclusive. The angle between the straight line L and the fourth plane δ is 74° to 80° inclusive, preferably 75° to 79° inclusive.

The operation of the bone plate 1 and the bone plate system 2 according to this embodiment with the above-described structure will be described below.

In order to perform high tibial osteotomy of gonarthrosis by using the bone plate system 2 according to this embodiment, a notch is formed from the inner side surface towards the outer side of the tibia X in a direction tilted relative to the longitudinal axis of the tibia X, and then the notch is dilated using a predetermined instrument. Thereafter, as shown in FIG. 1A, the body section 1a of the bone plate 1 is applied to an obliquely anterior inner side surface of the tibia X while the wedge-shaped artificial bone 4 is inserted in a dilated section 8, which has been dilated, and the bone plate 1 is placed on the tibia X so as to span the dilated section 8. More specifically, as shown in FIG. 1A, the transverse section 1b and the joining section 1c are applied to an upper inner side surface of an upper cut surface Y1 of the notch, and the body section 1a is applied to an upper inner side surface of a lower cut surface Y2 of the notch.

After the wedge-shaped artificial bone 4 is inserted into the dilated section 8, the screws 3 are made to pass through the screw holes 5, 6, and 7 from the outer side towards the inner side in the plate thickness direction to tighten the screws 3 into the tibia X. Thus, by means of the bone plate 1 fixed with the screws 3 so as to span the notch and the artificial bone 4 inserted into the dilated section 8, the tibia X above and below the dilated notch can support a vertical load W applied in a direction in which the notch is shrunk.

As shown in FIGS. 1B and 1C, the screw 3c inserted into the screw hole 5a of the body section 1a and the screw 3b inserted into the screw hole 7 of the joining section 1c are tightened into the tibia X at positions that are on planes substantially parallel to each other and that are twisted relative to each other. For this reason, not only do the axial line A of the screw 3b and the axial line B of the screw 3c that are projected on the articular surface of the tibia X intersect each other, but also the axial line A and the axial line B are substantially parallel to each other when the tibia X provided with the bone plate 1 is viewed from the front or the back.

By doing so, directly below the lower cut surface Y2 of the notch, the leading end of the screw 3c inserted into the screw hole 5a in the body section 1a is tightened in a direction in which this leading end moves away from the lower cut surface Y2, as shown in FIG. 1A. For this reason, the leading end of the screw 3c is prevented from breaking through the lower cut surface Y2 and sticking into the artificial bone 4. This allows a wide correction angle.

The bone plate can be fixed to the tibia while avoiding portions with low bone density and important tissue such as the popliteal artery.

According to the bone plate 1 of this embodiment, the body section 1a and the transverse section 1b that are fixed to the tibia X with the dilated section 8 interposed therebetween are arranged at positions twisted relative to each other by means of the joining section 1c. Thus, the body section 1a is fixed to an obliquely anterior inner side surface of the tibia X, whereas the transverse section 1b is fixed to the inner side surface of the tibia X. Consequently, even though the tibia X is subjected to the vertical load W when the patient equipped with the bone plate 1 for correction stands upright or walks, the bone plate 1 can be prevented from bending in the plate thickness direction.

For this reason, the bone plate 1 can be prevented from bulging towards the outer side relative to the head of the tibia, thereby preventing pain due to irritation to the skin resulting from bulging of the bone plate 1.

After the bone plate 1 and the screws 3 are removed after correction is completed, the screw holes remain open in the tibia X, possibly causing the load strength of the tibia to decrease, which may lead to fracturing of the cancellous bone. In this embodiment, however, because the screw holes remain at twisted positions in the tibia X, the vertical load W applied to the tibia can be distributed, and there is an advantage in that the possibility of causing fracturing of the cancellous bone can be reduced compared with, for example, a case where screw holes are formed in the tibia X at positions that are not twisted relative to each other.

Because the screws are threaded so that the axial lines D of the screw holes 6, the axial line A of the screw hole 7, and the axial line B of a screw hole 5a are each substantially in the plate thickness direction of the bone plate 1, the screws 3 can be firmly tightened to the tibia X through the bone plate 1 with an appropriate thickness, thereby further enhancing the fixability of the bone plate 1 to the tibia X.

Figure 4A:
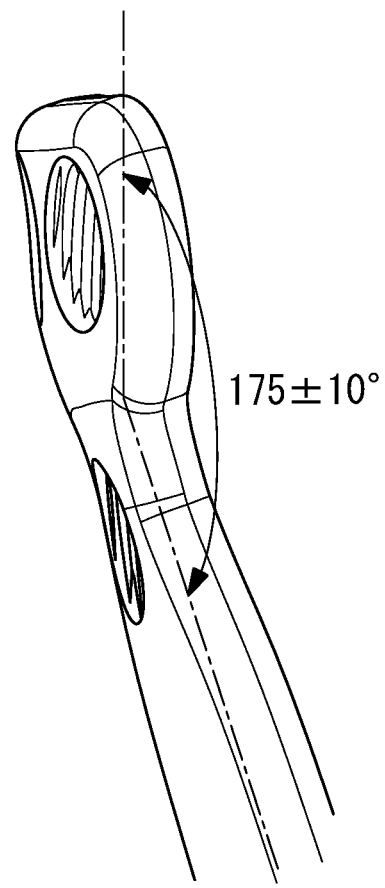
FIG. 4A is a partially magnified view of a side view of a transverse section and a joining section.

As shown in FIG. 4A, the joining section 1c is formed to bend with a bending angle of 175°±10° relative to the transverse section 1b. For this reason, as shown in FIG. 4B, the axial line A of the screw 3b inserted into the screw hole 7 in the joining section 1c is inserted upwardly by an amount equivalent to a bending angle of 175°±10 relative to the axial lines D of the screws 3a inserted into the screw holes 6 in the transverse section 1b.

With this structure, the fittability of the bone plate 1 to the tibia X can be enhanced while still preventing the leading end of the screw 3b inserted into the joining section 1c from interfering with the leading ends of the screws 3a inserted into the transverse section 1b.

By forming the bone plate 1 according to this embodiment into a gentle C shape from the body section 1a to the joining section 1c, the fittability of the bone plate 1 to the tibia can be enhanced further and optimized so that the screws do not break through the bone cutting surface and soft tissue posterior to the tibia.

For example, in the embodiment shown in FIG. 2A, the bone plate 1 is formed into a gentle C shape by setting, to 165°±10°, the angle between a straight line connecting the center of the screw hole 5a from the lower end of the body section 1a and a straight line connecting the center of the joining section 1c from the center of the screw hole 5a. The fittability to the tibia is further enhanced by setting, to 93°±10°, the angle between a straight line connecting the center of the joining section 1c from the center of the screw hole 5a and a straight line that specifies the arrangement direction of the plurality of (three in FIG. 2A) screw holes 6 provided in the transverse section 1b.

Because the body section 1a, the joining section 1c, and the transverse section 1b form a curved surface shape continuing in such a manner as to twist about an axial line parallel to the longitudinal direction of the tibia, the bone plate 1 can be placed in conformance to the side surface shape of the tibia X.

As shown in FIG. 2C, taking into account the side surface shape of the tibia X, the curved surface shape is desirably a shape twisted by 18.7°±10° about an axial line parallel to the longitudinal axis of the body section 1a.

Conventionally, there has been no choice but to use short screws 3 because the screws 3 were tightened in a direction in which the thickness of the tibia X is not so large. According to this embodiment, however, long screws 3 can be tightened in a direction in which the thickness of the tibia X is large, and hence there is also an advantage in that, even in a case where the bone quality is poor due to osteoporosis etc. and the fixing conditions are bad, the fixability can be enhanced while preserving the cancellous bone in a good state.

As shown in FIGS. 4A and 4B, the joining section 1c is formed to bend by an angle of, for example, 175°±10° relative to the transverse section 1b, and thereby, the leading end of the screw 3b inserted into the screw hole 7 in the joining section 1c can be prevented from interfering with the leading ends of the screws 3a inserted into the screw holes 6 in the transverse section 1b.

The bone plate 1 used in this embodiment has a total longitudinal length of 90 mm to 110 mm inclusive and preferably has a total longitudinal length of 95 mm to 105 mm inclusive. The distance between the screw hole 7 and the screw hole 5a is 24 mm to 34 mm inclusive and is preferably 24 mm to 30 mm inclusive.

By doing so, the bone plate 1 can be placed so as to closely fit to the inner side surface of the tibia X, regardless of differences in the length of the tibia X due to differences in the body build of the patient or differences in the amount of correction.

Because the distance between the screw hole 7 in the joining section 1c and the screw hole 5a in the body section 1a is large compared with a conventional bone plate 1, it is easy to accommodate a patient with a long tibia X. The bone plate 1 can also be fixed to a patient with a short tibia X without causing the bone plate 1 to bulge outwardly in the vicinity of the bone cutting surface, and hence it is possible to prevent pain resulting from the bone plate 1 bulging and irritating the skin.

The bone plate 1 used in the embodiment of the present application has a plate thickness of 3±1 mm. The bone plate 1 is designed so that the amount of flexure of the bone plate 1 in the longitudinal axis direction when the vertical load W in the longitudinal axis direction is applied to a position 30 to 50 mm away from the transverse section 1b of the bone plate 1 in a longitudinal axis direction of the transverse section in a state where the bone plate 1 is tightened after an empty space has been formed by dilating the tibia X between the screw hole 7 and the screw hole 5a falls within a range of 0.15 mm±0.1 mm/kgf.

By adjusting the amount of flexure of the bone plate 1 in this manner, it is possible to suppress stress shielding (a phenomenon in which a bone is readily free from load) for the tibia X provided with the bone plate 1 for correction thereby making it possible to further promote bone reproduction in the dilated section 8 into which the artificial bone 4 is inserted.

Because the screw 3b and the screw 3c tightened into the tibia X are formed so as to intersect each other when projected on the articular surface of the tibia X, the direction in which the load W acts can be distributed even though the vertical load W acts on the tibia X of a patient equipped with the bone plate 1 for correction, allowing the load to be effectively accommodated. For example, the intersecting angle of the screws is preferably 5° to 25° and desirably 10° to 20° or less.

The bone plate 1 and the screws 3 are formed of a highly biocompatible metal material. Such a material has relatively high safety to the human body even in a case where it is disposed on the human body.

As a biocompatible material used for the bone plate 1 and the screws 3, a titanium-based alloy ensuring sufficient strength and elasticity for a long time period is optimal. It is needless to say that the biocompatible material is not limited to a titanium alloy but can be realized by other materials including a cobalt-chromium alloy, stainless steel, etc.

Figure 5A:
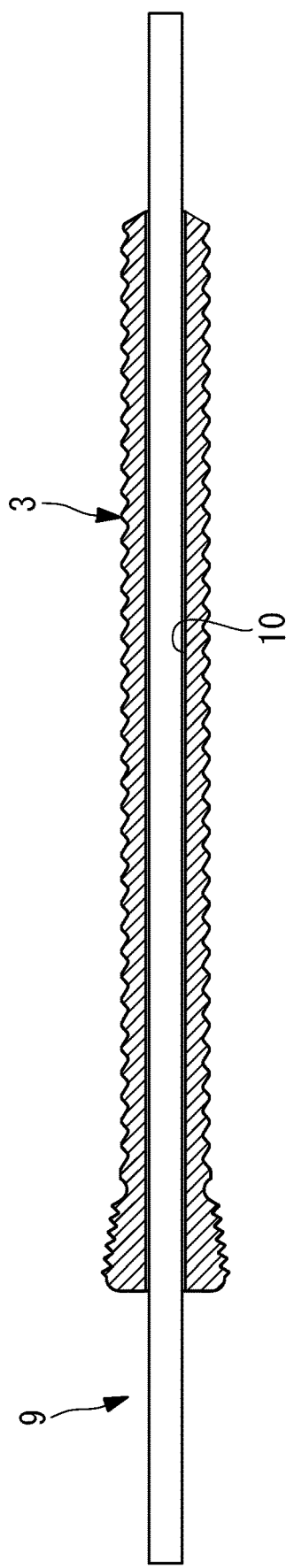
FIG. 5A is a diagram showing a case where a guide pin is inserted into a screw used in the bone plate system in FIG. 1.
Figure 5B:
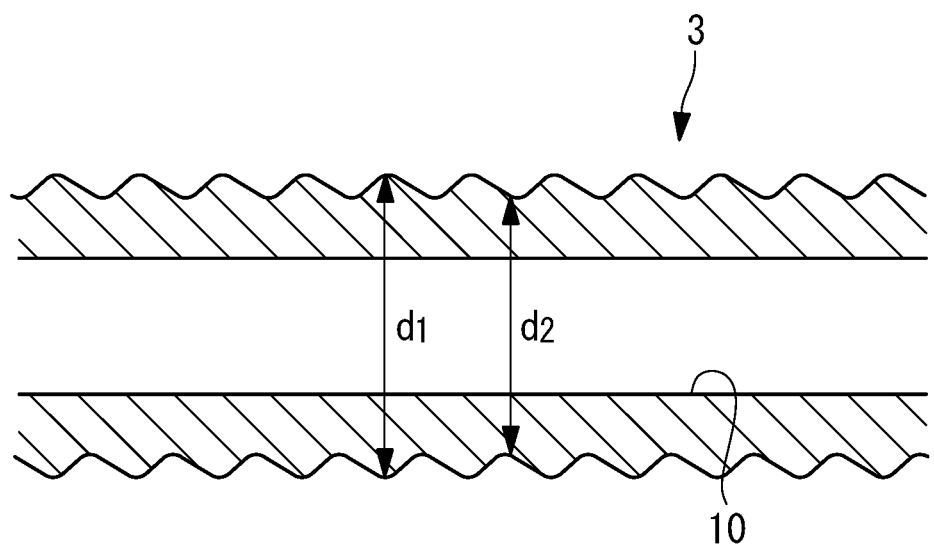
FIG. 5B is a magnified view of the screw head in FIG. 5A.

As shown in FIGS. 5A and 5B, each of the screws 3 according to this embodiment is a hollow screw 3 having a through-hole 10 that allows a guide pin 9 to pass therethrough, and for the screw 3, the crest diameter $d_1$ may be φ5.0 mm to 5.8 mm inclusive, the root diameter $d_2$ may be φ4.5 mm to 5.3 mm inclusive, and the hollow axis diameter $d_3$ of the screws 3 may be φ1.8 mm to 2.8 mm inclusive.

The screws 3 according to this embodiment are each designed to have a thickness large enough to accommodate the load W in the vertical direction without breaking, assuming that the bone plate 1 is fixed to the tibia X for a long time period on the order of years. With the settings within the ranges described above, the fixability can be enhanced as a result of a bone entering the leading end portion of a hollow hole, for example, in the epiphyseal region.

Because the screws 3 are not excessively thick, adverse effects of the screw holes that remain in the cancellous bone of the tibia X after the bone plate 1 has been removed can be minimized.

Because the body section 1a and the transverse section 1b of the bone plate 1 are arranged to be twisted relative to each other, the tightening directions of the screws 3 are not uniform, which may easily cause the screws to be fixed in incorrect directions. In this embodiment, however, because each of the screws 3 has the through-hole 10 that allows the guide pin 9 to pass therethrough, the screw 3 can be tightened by using the through-hole 10 formed in the screw 3 and the guide pin 9 as a guide, making it possible to enhance the work efficiency.

As shown in FIG. 1B, by setting the angle between the fourth plane δ and a straight line connecting the longitudinal-direction upper-end portion and lower-end portion in the bone plate 1 to 74° to 80° inclusive, preferably 75° to 79° inclusive, the bone plate 1 can be placed so as to closely fit to the inner side surface of the tibia X, regardless of differences in the length of the tibia X due to differences in the size of the body build of the patient and differences in the amount of correction. The screws 3 can be inserted into optimal areas where the screws do no break through the articular surface or interfere with the artificial bone 4 and a bone defect part.

Figure 6:
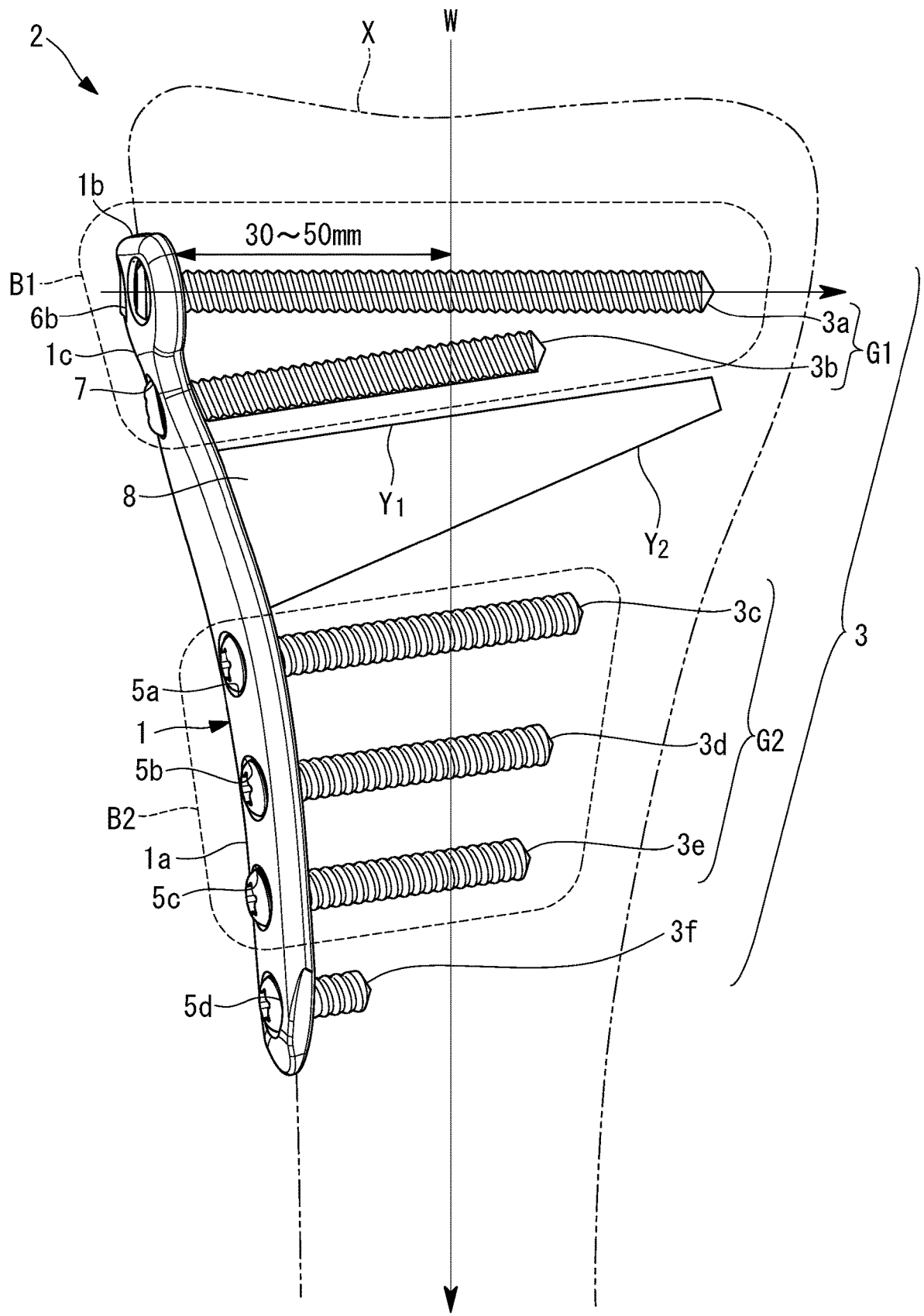
FIG. 6 is an overall view showing a modification of the bone plate in FIG. 1.
Figure 7:
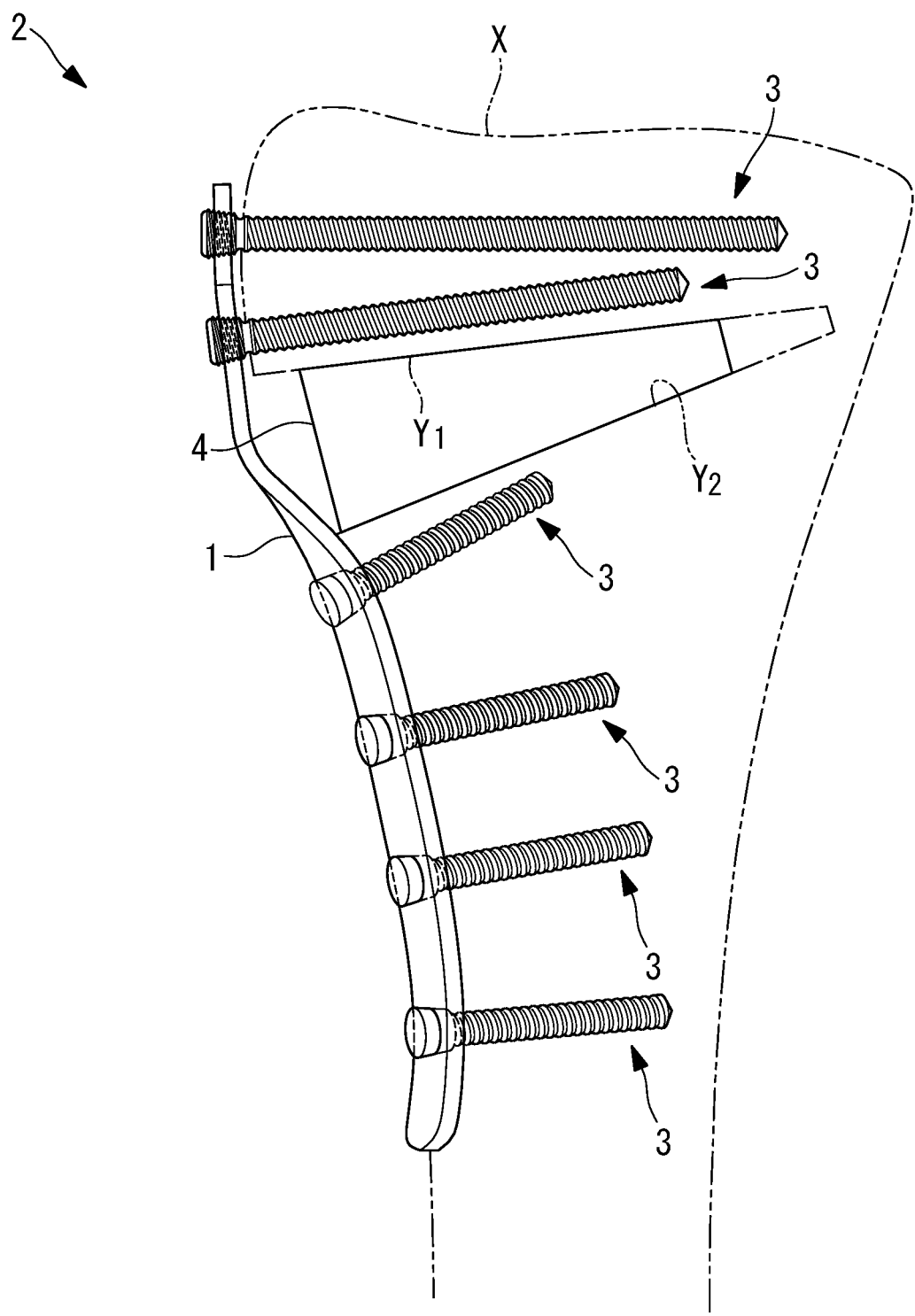
FIG. 7 is an overall view showing a bone plate system according to the prior art.

As shown in FIG. 6, a rigid first block B1 including the transverse section 1b, the joining section 1c, and a first screw group G1 composed of a plurality of screws 3 tightened into the screw holes 6 and 7, as well as a rigid second block B2 including the body section 1a and a second screw group G2 composed of a plurality of screws 3 tightened into the screw holes 5a and 5c, may be specified; the first block B1 and the second block B2 may be separated so as to form an empty space therebetween; and a bone plate system having elasticity that, when the vertical load W is relatively applied from the first block B1 to the second block B2 at a position 30 to 50 mm away from the transverse section 1b of the bone plate 1 in the first block B1 in the longitudinal axis direction of the transverse section, allows flexure with which the first block B1 is displaced by 0.15 mm±0.1 mm/kgf relative to the second block 2B in the vertical load direction may be designed. As shown in FIG. 1B, the transverse section 1b of the bone plate 1 preferably deflects in a direction in which the transverse section 1b rotates about a straight line for specifying the arrangement direction of the screw holes 6a, 6b, and 6c. However, the transverse section 1b of the bone plate 1 may deflect in a direction in which the joining section easily deflects.

Such a design also can enhance the effect of suppressing stress shielding for the tibia X provided with the bone plate 1 for correction.

As a result, the following aspect is read from the above described embodiment of the present invention.

One aspect of the present invention is a bone plate including: a band-shaped body section that is fixed along a longitudinal direction of a tibia screw holes that are arranged in the transverse section, the body section, and the joining section in a manner spaced apart from one another and that pass therethrough in a plate thickness direction, wherein the plurality of screw holes include a first screw hole provided in the joining section and a second screw hole provided in the body section, the body section, the joining section, and the transverse section have a curved surface shape that continues in such a manner as to twist about an axial line along the longitudinal direction of the tibia, a first plane on which an axial line of the first screw hole is disposed and a second plane on which an axial line of the second screw hole is disposed are substantially parallel to each other, the angles between a straight line connecting a longitudinal-direction upper-end portion and lower-end portion in the bone plate and the first plane and the second plane are predetermined angles, and the axial line of the first screw hole and the axial line of the second screw hole are disposed at twisted positions.

According to this aspect, the first plane having the axial line of the screw tightened into first screw hole and the second plane including the axial line of the screw tightened into the second screw hole are substantially parallel, and the axial line of the screw tightened into the first screw hole and the axial line of the screw tightened into the second screw hole are at positions twisted relative to each other.

The screw inserted into the first screw hole provided in the joining section is inserted so as to be substantially parallel to the bone cutting surface directly above the bone cutting surface at the site of osteotomy. Also, the screw inserted into the second screw hole provided in the body section is inserted so as to be substantially parallel to the screw inserted into the first screw hole directly below the site of osteotomy.

At this time, the leading end of the screw inserted into the body section disposed directly below the site of osteotomy is tightened in a direction which is not parallel to the osteotomy surface at the site of osteotomy, in other words, a direction gradually away from the osteotomy surface at the site of osteotomy, and hence a wide correction angle can be ensured without causing the leading end of the screw to break through the osteotomy surface.

After the screws have been removed, empty spaces are formed in the cancellous bone because the screw holes remain open at the positions where the screws were tightened, and this decreases the load strength of the tibia. In the embodiment of the present application, however, because the formed screw holes are at twisted positions, a load applied to the tibia in the vertical direction can be distributed, compared with a case where the screw holes are at positions not twisted relative to one another, thereby preventing fracturing of the cancellous bone.

The body section, the joining section, and the transverse section have a curved surface shape that continues in such a manner as to be twisted about an axial line parallel to the longitudinal direction of the tibia, and hence the bone plate can be placed in conformance to the side surface shape of the tibia.

Because a long screw can be tightened in a direction in which the thickness of the tibia is large, the fixability can be thereby enhanced.

The above-described aspect may further have: a third screw hole that is disposed in a manner spaced apart from the second screw hole in a longitudinal axis direction of the body section, wherein a third plane on which an axial line of the third screw hole is disposed may be substantially parallel to each of the first plane and the second plane.

By doing so, not only the first plane and the second plane, but also the third plane having the axial line of the screw tightened into the third screw hole, become substantially parallel to one another, and hence, with reference to the screw inserted into the third screw hole, an operator can easily visually recognize the directions of screws, which helps avoid incorrect insertion direction, thereby making it possible to more firmly tighten the bone plate to the tibia.

The above-described aspect may further include: a plurality of fourth screw holes that are provided in the transverse section and that are disposed in a manner spaced apart from one another in a direction intersecting a longitudinal direction of the body section, wherein the axial line of the first screw hole may be disposed along the first plane, which is tilted relative to a fourth plane including a straight line for specifying an arrangement direction of the plurality of fourth screw holes and the axial directions of the fourth screw holes.

By doing so, the leading end of the screw inserted into the first screw hole provided in the joining section is inserted in a tilted manner so as to approach the leading ends of the screws inserted into the four screw holes provided in the transverse section, and hence the bone plate can be more firmly screwed and fixed to the tibia.

In the above-described aspect, the axial line of the first screw hole, the axial line of the second screw hole, axial lines of the third screw holes, and the axial lines of the fourth screw holes may be arranged so as to be substantially in the plate thickness direction of the bone plate. With this structure, the screws can be firmly tightened to the bone plate having an appropriate thickness, and the fixability of the bone plate to the tibia can be further enhanced.

In the above-described aspect, the curved surface shape maybe twisted by 18.7°±10° about an axial line parallel to a longitudinal axis of the body section.

With this structure, the bone plate can be disposed so as to closely fit to the side surface of the tibia.

In the above-described aspect, the joining section may be formed to bend relative to the transverse section, and the bending angle of the joining section relative to the transverse section may be 175°±10°.

With this structure, the fittability of the bone plate to the tibia can be enhanced while preventing the leading end of the screw inserted into the joining section from interfering with the leading ends of the screws inserted into the transverse section. Because large distances can be ensured from the vicinity of the bone cutting surface, which is easily subjected to a bone fracture, to the screws, the bone plate can be fixed stably.

In the above-described aspect, the total length in the longitudinal direction may be 90 mm to 110 mm inclusive and may be desirably 95 mm to 105 mm inclusive, and the distance between the first screw hole and the second screw hole may be 24 mm to 34 mm inclusive and may be desirably 24 mm to 30 mm inclusive.

By doing so, the bone plate can be placed so as to closely fit to the inner side surface of the tibia, regardless of differences in the length of the tibia due to differences in the body build of the patient or differences in the amount of correction.

Because the distance between the first screw hole and the second screw hole is large compared with the spacing between screw holes in a conventional bone plate, it is easy to accommodate a patient with a long tibia X. Furthermore, the bone plate can also be fixed to a patient with a short tibia without causing the bone plate to bulge outwardly in the vicinity of the bone cutting surface, and hence it is possible to prevent pain resulting from the bone plate bulging and irritating the skin. Because large distances can be ensured from the vicinity of the bone cutting surface, which is easily subjected to a bone fracture, to the screws, the bone plate can be fixed stably.

In the above-described aspect, the plate thickness of the bone plate may be 3±1 mm, and the amount of flexure of the bone plate when a vertical load in the longitudinal axis direction is applied at a position 30 to 50 mm away from the transverse section of the bone plate in the longitudinal axis direction of the transverse section in a state where the bone plate is tightened with the plurality of screws may be 0.15 mm±0.1 mm/kgf.

By adjusting the amount of flexure of the bone plate in this manner, stress shielding (a phenomenon in which a bone is readily free from load) for the tibia provided with the bone plate can be suppressed, thereby making it possible to further promote bone reproduction in the dilated section into which the artificial bone is inserted.

Another aspect of the present invention is a bone plate system including: any one of the above-described bone plats; and a plurality of screws that are tightened into the plurality of screw holes in the bone plate to fix the bone plate to the tibia.

According to the above-described aspect, the screw tightened into the first screw hole and the screw tightened into the second screw hole are disposed on planes substantially parallel to each other such that the axial line of the first screw and the axial line of the second screw are at twisted positions, and hence the leading end of the screw tightened into the second screw hole is tightened in a direction gradually away from the osteotomy surface at the site of osteotomy, and a wide correction angle can be ensured without causing the screw to break through the osteotomy surface.

By tightening the screws in this manner, the screws can be tightened while avoiding portions with low bone density and important tissue such as the popliteal artery.

Because the bone plate can be prevented from bulging towards the outer side relative to the head of the tibia, it is possible to prevent pain due to irritation to the skin resulting from bulging of the bone plate.

Even in a case where a load is applied in the vertical direction as a result of the patient equipped with the plate walking etc., the direction in which the load is applied can be distributed, allowing the load to be effectively accommodated.

Because the axial directions of the screw holes in the cancellous bone of the tibia after the removal of the screws are twisted relative to one another, the load in the vertical direction applied to the tibia can be distributed, compared with a case where the axial directions of the screw holes are not twisted, thereby preventing fracturing of the cancellous bone.

Because the screws can be tightened in a direction in which the thickness of the tibia is large, long screws can be used, and thereby the fixability can be enhanced.

In the above-described aspect, the bone plate and the screws may be formed of a highly biocompatible material and may be preferably formed of a titanium-based alloy, a cobalt-chromium alloy, or a stainless steel.

In this manner, an implant of a material that has sufficient strength and elasticity and that is highly biocompatible can be used.

In the above-described aspect, the screws may be hollow screws each having a through-hole that allows a guide pin to pass therethrough, each of the screws may have a crest diameter of φ5.0 mm to 5.8 mm inclusive and a root diameter of φ4.5 mm to 5.3 mm inclusive, and the hollow axis diameter of the above-described hollow screw may be φ1.8 mm to 2.8 mm inclusive.

In the above-described aspect, assuming that the bone plate is screwed and fixed to the tibia with screws for a long time period on the order of years, the screws are each designed to have a thickness large enough to accommodate the load in the vertical direction without breaking. With the settings within the ranges described above, the fixability can be enhanced as a result of a bone entering the leading end portion of a hollow hole, for example, in the epiphyseal region.

Adverse effect by the screw holes that remain in the cancellous bone of the tibia after the bone plate has been removed can be minimized.

Because the body section and the transverse section of the bone plate are arranged to be twisted relative to each other, the tightening directions of the screws are not uniform, which may easily cause the screws to be fixed in incorrect directions. In the above-described aspect, however, because each of the screws has the through-hole that allows the guide pin to pass therethrough, the screw can be tightened by using the through-hole formed in the screw and the guide pin as a guide, making it possible to enhance the work efficiency.

In the above-described aspect, the angles between the straight line connecting the longitudinal-direction upper-end portion and lower-end portion in the bone plate and the first plane and the second plane may be 80° to 95° inclusive and may be preferably 84° to 91° inclusive, and the angle relative to the fourth plane may be 74° to 80° inclusive and may be preferably 75° to 79° inclusive.

With this structure, the bone plate can be placed so as to closely fit to the inner side surface of the tibia, regardless of differences in the length of the tibia due to differences in the size of the body build of the patient or differences in the amount of correction.

The screws can be inserted into optimal areas where the screws do no break through the articular surface or interfere with the artificial bone and a bone defect part.

The above-described aspect may include: a first block containing the transverse section, the joining section, and a first screw group composed of a plurality of screws tightened into the first screw hole and the fourth screw holes; and a second block containing the body section and a second screw group composed of a plurality of screws tightened into the second screw hole and the third screw hole, wherein the bone plate system may have elasticity that, when a vertical load is relatively applied from the first block to the second block at a position 30 to 50 mm away from the transverse section of the bone plate in the longitudinal axis direction, allows flexure with which the first block is displaced by 0.15 mm±0.1 mm/kgf relative to the second block in a direction of the vertical load.

By adjusting the amount of flexure of the bone plate system in this manner, stress shielding (a phenomenon in which a bone is readily free from load) for the tibia provided with the bone plate can be suppressed, thereby making it possible to further promote bone reproduction in the dilated section into which the artificial bone is inserted.

REFERENCE SIGNS LIST

1 Bone plate
1a Body section
1b Transverse section
1c Joining section
2 Bone plate system
3 Screw
3b Screw (first screw)
3c Screw (second screw)
4 Artificial bone (artificial bone member)
5 Screw hole
5a Screw hole (second screw hole)
5c Screw hole (third screw hole)
6 Screw hole (fourth screw hole)
7 Screw hole (first screw hole)
8 Dilated section
9 Guide pin
10 Through-hole
X Tibia
First axial line A
Second axial line B
Third axial line C
Fourth axial line D
First plane α
Second plane β
Third plane γ
Fourth plane δ
First screw group G1
Second screw group G2
First block B1
Second block B2

The invention claimed is:

1. A bone plate system comprising:
a bone plate having a plurality of screw holes, and
a plurality of screws that are tightened into the plurality of screw holes in the bone plate to fix the bone plate to a tibia,
the bone plate comprising:
a band-shaped body section configured to be fixed, along a longitudinal direction of the tibia, to an obliquely anterior inner side surface of the tibia at a position on a first side of a notch formed in the inner side surface of the tibia;
a transverse section configured to be fixed, along a direction intersecting the longitudinal direction of the tibia, to the inner side surface of the tibia at a position on a second side of the notch, the second side being closer to a head of the tibia than the first side;
a joining section for joining the body section and the transverse section; and
the plurality of screw holes arranged in the transverse section, the body section, and the joining section in a manner spaced apart from one another and that pass through the plate in a plate thickness direction,
wherein the plurality of screw holes include a first screw hole provided in the joining section and a second screw hole provided in the body section,
the body section, the joining section, and the transverse section have a curved surface shape that continues in such a manner as to twist about an axial line along the longitudinal direction of the tibia, a first plane on which an axial line of the first screw hole is disposed and a second plane on which an axial line of the second screw hole is disposed are substantially parallel to each other, angles between a straight line connecting a longitudinal-direction upper-end portion and lower-end portion in the bone plate and the first plane and the second plane are predetermined angles, the axial line of the first screw hole and the axial line of the second screw hole are disposed at twisted positions, the plate thickness of the bone plate is between 2 mm and 4 mm, and an amount of flexure of the bone plate and the plurality of screws when a vertical load along a longitudinal axis is applied to the plurality of screws at a position between 30 and 50 mm away from the transverse section of the bone plate in a direction of the longitudinal axis in a state where the bone plate is tightened with the plurality of screws is between 0.05 mm and 0.25 mm when the vertical load is 1 kilogram.

2. The bone plate system according to claim 1, further comprising:

a third screw hole that is disposed in a manner spaced apart from the second screw hole in a longitudinal axis direction of the body section, wherein a third plane on which an axial line of the third screw hole is disposed is substantially parallel to each of the first plane and the second plane.

3. The bone plate system according to claim 2, further comprising:

a plurality of fourth screw holes that are provided in the transverse section and that are disposed in a manner with a space between each of the plurality of fourth screw holes in an arrangement direction intersecting the longitudinal axis direction of the body section, wherein the axial line of the first screw hole is disposed along the first plane, which is tilted relative to a fourth plane including a straight line for specifying the arrangement direction of the plurality of fourth screw holes and directions of axial lines of the fourth screw holes.

4. The bone plate system according to claim 3, wherein the axial line of the first screw hole, the axial line of the second screw hole, the axial line of the third screw hole, and the axial lines of the fourth screw holes are arranged so as to be substantially in the plate thickness direction of the bone plate.

5. The bone plate system according to claim 3, wherein the angles between the straight line connecting the longitudinal-direction upper-end portion and lower-end portion in the bone plate and the first plane and the second plane are between 80° and 95° inclusive, and an angle between the straight line connecting the longitudinal-direction upper-end portion and lower-end portion in the bone plate and the fourth plane is between 74° and 80° inclusive.

6. The bone plate system according to claim 1, wherein the curved surface is twisted by between 8.7° and 28.7° about an axial line parallel to a longitudinal axis of the body section.

7. The bone plate system according to claim 1, wherein the joining section is formed at an angle between 165° and 185° relative to the transverse section.

8. The bone plate system according to claim 1, wherein the total length in the longitudinal direction is between 90 mm and 110 mm inclusive, and the distance between the first screw hole and the second screw hole is between 24 mm and 34 mm inclusive.

9. The bone plate system according to claim 1, wherein the bone plate and the screws are formed of a highly biocompatible material.

10. The bone plate system according to claim 9, wherein the highly biocompatible material is selected from a group consisting of a titanium-based alloy, a cobalt-chromium alloy, and a stainless steel.

11. The bone plate system according to claim 1, wherein the plurality of screws are hollow screws each having a through-hole that allows a guide pin to pass through, each of the plurality of screws has a crest diameter of between 5.0 mm and 5.8 mm inclusive and a root diameter of between 4.5 mm and 5.3 mm inclusive, and a diameter of the through-hole of each hollow screw is between 1.8 mm and 2.8 mm inclusive.

12. The bone plate system according to claim 1 comprising:

a first block containing the transverse section, the joining section, and a first screw group composed of the plurality of screws tightened into the first screw hole and fourth screw holes in the transverse section; and a second block containing the body section and a second screw group composed of the plurality of screws tightened into the second screw hole and a third screw hole in the body section, wherein the bone plate system has elasticity that, when the vertical load is relatively applied from the first block to the second block at the position 30 to 50 mm away from the transverse section of the bone plate in the direction of the longitudinal axis, allows flexure with which the first block is displaced by between 0.05 mm and 0.25 mm when the vertical load is 1 kilogram relative to the second block in a direction of the vertical load.

13. A bone plate system comprising:

a bone plate having a plurality of screw holes, and a plurality of screws that are tightened into the plurality of screw holes in the bone plate to fix the bone plate to a tibia, the bone plate comprising:

a band-shaped body section configured to be fixed, along a longitudinal direction of the tibia, to an obliquely anterior inner side surface of the tibia at a position on a first side of a notch formed in the inner side surface of the tibia;

a transverse section configured to be fixed, along a direction intersecting the longitudinal direction of the tibia, to the inner side surface of the tibia at a position on a second side of the notch, the second side being closer to a head of the tibia than the first side;

a joining section for joining the body section and the transverse section; and the plurality of screw holes arranged in the transverse section, the body section, and the joining section in a manner spaced apart from one another and that pass through the plate in a plate thickness direction, wherein the plurality of screw holes include a first screw hole provided in the joining section and a second screw hole provided in the body section, the body section, the joining section, and the transverse section have a curved surface shape that continues in such a manner as to twist about an axial line along the longitudinal direction of the tibia, a first plane on which an axial line of the first screw hole is disposed and a second plane on which an axial line of the second screw hole is disposed are substantially parallel to each other, angles between a straight line connecting a longitudinal-direction upper-end portion and lower-end portion in the bone plate and the first plane and the second plane are predetermined angles, the axial line of the first screw hole and the axial line of the second screw hole are disposed at twisted positions, wherein the bone plate system has elasticity that, when a vertical load is relatively applied from a first block, containing the transverse section, the joining section, and a first screw group composed of the plurality of screws tightened into the first screw hole and fourth screw holes in the transverse section, to a second block, containing the body section and a second screw group composed of the plurality of screws tightened into the second screw hole and a third screw hole in the body section, along a longitudinal axis at a position between 30 and 50 mm away from the transverse section of the bone plate in a direction of the longitudinal axis, allows flexure with which the first block is displaced relative to the second block by between 0.05 mm and 0.25 mm when the vertical load is 1 kilogram in a direction of the vertical load.

* * * * *

UNITED STATES PATENT AND TRADEMARK OFFICE
CERTIFICATE OF CORRECTION

PATENT NO. : 10,932,831 B2  
APPLICATION NO. : 16/180128  
DATED : March 2, 2021  
INVENTOR(S) : Kuroda et al.

Page 1 of 1

It is certified that error appears in the above-identified patent and that said Letters Patent is hereby corrected as shown below:

On the Title Page

(73) Assignee should read: OLYMPUS TERUMO BIOMATERIALS CORP., TOKYO (JP)

Signed and Sealed this  
Thirtieth Day of November, 2021

Drew Hirshfeld  
*Performing the Functions and Duties of the*  
*Under Secretary of Commerce for Intellectual Property and*  
*Director of the United States Patent and Trademark Office*